US006488708B2

(12) United States Patent
Sarfarazi (10) Patent No.: US 6,488,708 B2
(45) Date of Patent: *Dec. 3, 2002

(54) OPEN CHAMBER, ELLIPTICAL, ACCOMMODATIVE INTRAOCULAR LENS SYSTEM

(76) Inventor: Faezeh Sarfarazi, 25 Wiswall Rd., Newton Center, MA (US) 02159

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/288,560

(22) Filed: Apr. 9, 1999

(65) Prior Publication Data

US 2002/0002404 A1 Jan. 3, 2002

(51) Int. Cl.⁷ .................................................. A61F 2/16
(52) U.S. Cl. ..................... 623/6.34; 623/6.37; 623/6.39
(58) Field of Search ............................... 623/6.37, 6.34, 623/6.36, 6.13, 6.32, 6.39, 6.11, 6.22, 6.38, 6.43, 6.46, 6.49, FOR 105

(56) References Cited

U.S. PATENT DOCUMENTS

| | | | |
|---|---|---|---|
| 4,253,199 A | 3/1981 | Banko | |
| 4,254,509 A | 3/1981 | Tennant | |
| 4,409,691 A | 10/1983 | Levy | |
| 4,426,741 A | 1/1984 | Bittner | |
| 4,463,458 A | 8/1984 | Seidner | |
| 4,575,373 A | 3/1986 | Johnson | |
| 4,790,847 A | 12/1988 | Woods | |

(List continued on next page.)

FOREIGN PATENT DOCUMENTS

| | | |
|---|---|---|
| EP | 0 162 573 A2 | 11/1985 |
| EP | 0 328 117 A2 | 8/1989 |
| EP | 0 337 390 A2 | 10/1989 |
| EP | 0 507 292 B1 | 10/1992 |
| EP | 0 507 292 A1 | 10/1992 |
| EP | 0 592 813 A1 | 4/1994 |

OTHER PUBLICATIONS

Hara et al., Accommodative Intraocular Lens with Spring Action Part 1. Design and Placement in an Excised Animal Eye. Ophthalmic Surgery. 1990; 21(2): 128–133.

(List continued on next page.)

*Primary Examiner*—David H. Willse
(74) *Attorney, Agent, or Firm*—William G. Lane (57) ABSTRACT

An open chamber, accommodative, intraocular lens method and apparatus operable to be positioned within an evacuated capsular bag of a human eye following extracapsular extraction of a natural crystalline lens is provided having an anterior refractive lens optic, a first haptic segment having a first end and being connected at said first end to a peripheral portion of said anterior lens optic and a second end and said haptic segment extending in an elliptical curve, in longitudinal cross-section, along the the line of sight of the lens and at least a second haptic segment having a first end and being connected at said first end to a peripheral portion of said lens optic and a second end and said at least a second haptic segment extending in an elliptical curve, in longitudinal cross-section, and being operably joined with the second end of said first haptic segment to form an open chamber, elliptical shaped haptic accommodating support for the anterior lens within an evacuated capsular bag of a human eye.

58 Claims, 5 Drawing Sheets

U.S. PATENT DOCUMENTS

| | | |
|---|---|---|
| 4,842,601 A | 6/1989 | Smith |
| 4,888,012 A | 12/1989 | Horn et al. |
| 4,892,543 A | 1/1990 | Turley |
| 4,902,293 A | 2/1990 | Feaster |
| 4,963,148 A | 10/1990 | Sulc et al. |
| 4,994,080 A | 2/1991 | Shepard |
| 4,994,082 A | 2/1991 | Richards et al. |
| 5,047,051 A | 9/1991 | Cumming |
| 5,108,429 A | 4/1992 | Wiley |
| 5,152,789 A | 10/1992 | Willis |
| 5,203,788 A | 4/1993 | Wiley |
| 5,275,623 A | 1/1994 | Sarfarazi |
| 5,275,624 A | 1/1994 | Hara et al. |
| 5,326,347 A | 7/1994 | Cumming |
| RE34,998 E | 7/1995 | Langerman |
| 5,476,514 A | 12/1995 | Cumming |
| 5,489,302 A | 2/1996 | Skottun |
| 5,496,366 A | 3/1996 | Cumming |
| 5,593,436 A | 1/1997 | Langerman |
| 5,628,795 A | 5/1997 | Langerman |
| 5,674,282 A | 10/1997 | Cumming |
| 5,728,155 A | 3/1998 | Anello et al. |
| 5,843,188 A | 12/1998 | McDonald |
| 6,013,101 A * | 1/2000 | Israel .................. 623/6.43 |

OTHER PUBLICATIONS

Grinberg, "Questioning Our Classical Understanding of Accommodation and Presbyopia", Amer. J. Optometry & Physiological Optics, 63(7):571–580.

Schachar, "Cause and Treatment of Presbyopia with a Method for Increasing the Amplitude of Accommodation", Ann. Ophthalmol. 1992; 24:445–452.

Schachar, Ann. Ophthal., 1993; 25:404–409.

Shachar, Ann. Ophthal., 1994; 26:4–9.

Koretz et al., "How the Human Eye Focuses", Sci. Amer., Jul. 1988, pp. 64–71.

* cited by examiner

OPEN CHAMBER, ELLIPTICAL, ACCOMMODATIVE INTRAOCULAR LENS SYSTEM

RELATED PATENT

This application is related in part to my prior U.S. Pat. No. 5,275,623 entitled "Elliptical Accommodative Intraocular Lens for Small Incision Surgery" dated Jan. 4, 1994.

BACKGROUND OF THE INVENTION

This invention relates to an improved, accommodative, intraocular lens system operable to be positioned within the interior of an evacuated capsular bag of a human eye. More specifically, this invention relates to an open accommodative, intraocular lens system method and apparatus operable to be inserted within an evacuated capsular bag of a human eye following extracapsular surgery to remove and replace a dysfunctional natural crystalline lens. The invention finds particular application in restoring multi-focal vision following cataract surgery, correction of myopia, correction of presbyopia and treatment of the symptoms of retinal damage, such as, age related macular degeneration of the human eye.

In the human eye, multi-focal vision is provided by a combination of a convex-concave lens, known as the cornea, positioned in front of the iris and a bi-convex lens positioned within a clear elliptical envelope behind the iris and in front of the vitreous humor of the eye. Accommodation of vision at both infinity and near vision of 250 mm is provided by a peripheral muscular body extending about the capsular bag and connected to the equator thereof by Zonula of Zinn which are thin strands attaching the equator of the capsular bag to the ciliary muscles of a human eye system. Tension and the relaxation of the ciliary muscles causes the capsular bag to lengthen or contract which varies the focus of the eye.

In certain instances at an early age, such as trauma or heredity, or in later stages of the life cycle, the natural crystalline lens of a human becomes cloudy and hardened, somewhat like milk glass, which occludes vision and results in eventual blindness. This condition is known as a cataract and was a major source of blindness in mankind for centuries. As early as 1766 Cassanova, in his memoirs, suggested that an intraocular lens could be implanted within a human eye to replace an opaque natural crystalline lens. It was not until 1949, however, that a Dr. Harold Ridley, at the Thomas Hospital in London, inserted the first intraocular lens within the eye of a woman of about 60 years of age following cataract extraction. Early IOLs, however, tended to dislocate, cause iris atrophy and in some instances secondary glaucoma. Attempts to overcome the early disadvantages of Dr. Ridley's solid posterior chamber lens included placement of a lens in the anterior chamber, in front of the iris. In addition Dr. Binkhorst of Holland invented an iris clip lens and Dr. Choyce an iris plane lens. However, both anterior chamber and iris fixed lenses created a risk of damages to delicate iris tissue.

An advanced in the intraocular lens art occurred when Dr. Shearing invented the first, practical, posterior chamber lens. Dr. Shearing's design included a bi-convex polymethylmethacrylate (PMMA) lens body which was positioned behind the iris and against the ciliary muscle or within the capsular bag. The Shearing IOL was maintained in a generally central axis of vision by thin strand haptics that extended radially from the peripheral edge of the lens optic and were curved at their distal ends. The curved portions of the haptics abutted against peripheral tissue of the eye to support the lens. Although the Shearing lens haptics had small arc contact zones, the success of the lens led other pioneers to develop a variety of haptic designs, such as, a C-loop or an S-loop and other designs to relieve trauma to adjacent contact tissue. A significant limitation of all fixed focus intraocular lens designs is that the focal point is fixed at infinity. Accordingly, for all near vision tasks, conventional reading glasses became necessary. In this connection, it is believed that several million pairs of reading glasses are sold annually within the United States alone.

In addition to the incidences of cataract formation and its attendant tendency to blindness, reductions in both amplitude and speed of accommodation with age are well known. This condition is known as presbyopia. The amplitude of accommodation decreases progressively with age from some 14 diopters in a child of ten years to near zero at age fifty or so. The exact explanation for the physiological phenomena is not well documented, however, it is observed that the curvatures of excised senile lenses were considerably less than those of juvenile ones. This failure could be due to a hardening of the lens material, sclerosis, decrease in modulus of elasticity, or to a decrease in thickness of the capsule or a combination of the above. Regardless of the cause, it is a recognized fact that beginning at about age 40–45 correction for both near and far vision becomes necessary in most humans. Conventional techniques include bifocal glasses, bifocal contact lenses, contact lenses for distance and reading glasses for near vision, and mono-focus contact lens sets where one eye carries a contact lens for distance vision and the other eye carries a contact lens for reading. Still further refractive surgery for distance vision coupled with reading glasses has been used successfully to correct presbyopia. Notwithstanding the grateful relief of being able to see clearly at both near and distance, all of the above solutions are compromises, in one form or another, and are dramatically more inconvenient than the natural bifocal vision of youth.

A somewhat related visual dysfunction in youth and young adults is mild to severe myopia or the loss of an ability to clearly focus at distance. Glasses, contact lenses or refractive surgery are the most common forms of accommodation, however, with certain cases of myopia it may be necessary to correct vision up to 30 to 40 diopters. As the degree of myopia increases the use of conventional solutions becomes less attractive and it would be highly desirable to be able to reliably correct this patient concern.

Still further, as humans age, or through viral inflammations or trauma, deterioration in retinal cells, including macular degeneration, can cause a dramatic loss of perception of light and color by rods and cones of the retina. In certain instances a degree of relief for humans suffering from impairment of vision from the loss of retinal cells can be achieved by increasing the intensity or magnification of images presented to healthy cells. In certain instances of macular degeneration it would be desirable to present a patient with an option of a correction of 30 to 70 diopters. This magnitude of correction is not readily achievable with presently known techniques.

The limitations to vision outlined in the proceeding are not intended to be exhaustive but are major concerns and represent limitations placed on mankind of impaired vision occasioned from trauma, disease, and/or age. It would be highly desirable if these limitations could be addressed and minimized or eliminated and thus restore to patients at least a portion of the accommodation and clarity of the vision of their youth.

OBJECTS OF THE INVENTION

It is a general object of the invention to provide a method and apparatus to obviate or minimize limitations to accommodated bifocal vision of the type previously described.

It is another object of the invention to provide an intraocular lens system which is operable to restore a patient's multi-focal vision following extracapsular cataract extraction.

It is a further object of the invention to provide an intraocular lens system which can be used as a replacement of a patient's natural crystalline lens to accommodate and offset presbyopia limited vision with age.

It is a related object of the invention to provide an intraocular lens system that can be used in place of a patient's natural crystalline lens to correct instances of mild to severe myopia.

It is yet another object of the invention to provide an intraocular lens system which can be used to improve vision in patients having retinal deterioration, such as, macular degeneration.

It is a specific object of the invention to provide an intraocular lens system that is operable to utilize the natural physiology of the human eye to restore accommodative multi-focal vision to a patient.

It is yet another object of the invention to restore a patient's vision following cataract surgery or for correction of presbyopia without using refractive surgery, contact lenses, or glasses as a part of the corrective solution.

It is still another object of the invention to provide an intraocular lens system solution to create a vision augmentation of 70 to 90 diopters without use of thick glasses or radical refractive surgery

SUMMARY OF THE INVENTION

In at least one preferred embodiment of the invention, intended to accomplish the above, and other, objects of the invention are achieved by an open chamber, accommodative, intraocular lens system operable to be positioned within the interior of an evacuated capsular bag of a human eye. The inventive intraocular lens system includes a first anterior lens optic and a second posterior lens optic which are arranged in axial alignment visually. An open chamber, haptic system is connected between the two lenses and in a preferred form three haptics segments are fashioned in the form of elliptical segments which are connected at their ends to the peripheral rims of the lens bodies and arc outwardly away from the visual axis of the lenses.

The overall cross-sectional shape of the inventive intraocular lens system is elliptical and is designed to fit smoothly within the interior of a patient's capsular bag. The elliptical haptic elements are flexible and as the capsular bag is peripherally pulled outwardly at its equator the bag contracts. This contraction is produced by a patient's natural vision accommodations by the ciliary muscles of the eye. In this, the anterior lens is moved axially toward the posterior lens to provide vision at infinity. As the ciliary muscles are constricted and move radially inward, for near vision accommodation, tension on connective zonula decreases and the patient's capsular bag thickens allowing the haptics to assume their natural memory state.

Although the use of a two optic lens system is preferred, wherein the anterior lens is bi-convex and the posterior lens is concavo-convex to provide a corrective range of accommodation of about 4 diopters following extracapsular cataract surgery, other lens embodiments are contemplated by the subject invention. In this, other lens cross-sectional configurations can be used, for example, concavo-planar or concavo-convex for either the anterior or posterior. lens. In still other instances it may be desirable to remove the posterior lens entirely or eliminate its optic function by using a biplanar lens body. Finally, the invention also envisions adding more than two lenses, such as three lenses, in instances where extreme dioptive correction is desirable.

In a preferred embodiment three elliptical haptic segments are use extending at an arc of about 40 degrees outwardly from the rims of the lens optics and are peripherally spaced around the periphery with 80 degree segments of open space. These haptic segments are elliptical in cross-section takes along a line of sight of the lens system and are fashioned in a natural state to have an elliptical ratio of 0.96. Other arrangements of the haptics are also envisioned such as two wider based haptics or four or more haptics that would be thinner in outer width. The underlying criteria is that the haptics are flexible enough to enable relatively unrestricted accommodation movement of the anterior lens toward the posterior chamber lens of about 1.9 mm or so in response to the natural movement of the ciliary muscle and zonula attached to the capsular bag while simultaneously being stiff enough to support a lens or lenses of the optic system in visual axial alignment within the capsular bag of a patient's eye.

BRIEF DESCRIPTION OF THE DRAWINGS

Other object and advantages of the present invention win become apparent from the following detailed description of preferred embodiments of the invention taken in conjunction with the accompanying drawings wherein.

DETAILED DESCRIPTION OF PREFERRED EMBODIMENTS OF THE INVENTION

Turning now to the drawings wherein like numerals indicate like parts, there will be seen preferred embodiments of the invention. Before describing the preferred embodiment, however, a brief statement about the context of the invention is believed appropriate.

Context of the Invention

Figure 1:
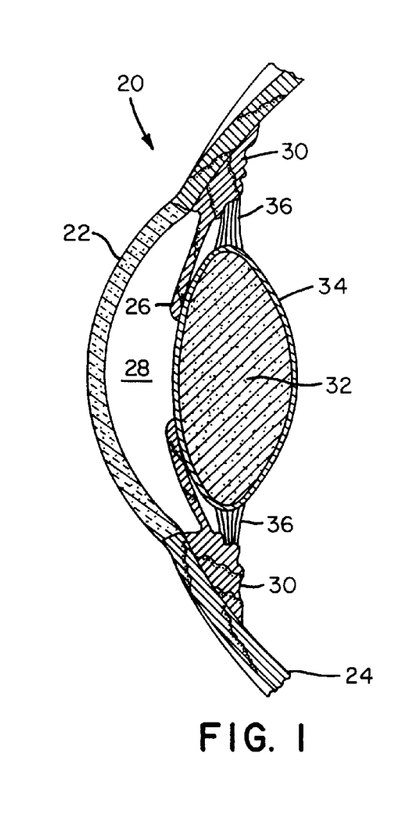
FIG. 1 is a partial cross-sectional view of a human eye including a lens system composed of a convex-concave cornea and an accommodative, bi-convex natural crystalline lens positioned within a posterior chamber capsular bag.

Turning now to FIG. 1 there will be seen a partial cross-sectional view of an anterior segment of a human eye 20. Vision in humans is provided by a first convex/concave lens known as a cornea 22. This segment is partially spherical and is transparent to light. The cornea 22 is connected at its perimeter to a generally spherical exterior body of the eye known as a sclera 24. An iris 26 is positioned within an anterior chamber of the eye 28 and serves to vary the amount of light permitted to pass into the eye structure. The iris 26 extends into and is joined with a muscular structure known as the ciliary body or muscle 30 which extends peripherally about an interior portion of the eye. A natural crystalline lens 32 is positioned behind the iris 26 and is enrobed by a capsular membrane or bag 34. The natural crystalline lens 32 approximates an ellipse in cross-section and is circular when viewed along a line of sight. Zonula of Zinn 36 extend between the ciliary muscle 30 and an equator position of the capsular bag 34. A hyloid face, not shown, extends across the posterior surface of the lens 32 and isolates the forward segment of the eye from a vitreous chamber filled with clear vitreous humor.

Light is focused by the human eye by being refracted through the cornea and then refracted again through the bi-convex natural crystalline lens and is focused on a retina at the base of the eye. Vision from infinity to 250 millimeters is accommodated by varying the shape of the natural crystalline lens 32. More specifically, images at infinity are focused by the ciliary muscle 30 relaxing which permits their peripheral expansion and thus tensioning the zonula 36. Tension of the zonula draws the equator of the capsular bag radially outward and foreshortens the thickness of the lens body 32, providing for distance vision. In contrast, near vision is accommodated in a human eye by the ciliary muscles contracting which releases tension on the zonula allowing the lens body 32 to thicken into its natural state and thus focusing near objects upon the retina for transmission to the brain by the optic nerve.

A human eye adapts readily to variations in focal length and seamlessly enables a human to view objects at infinity as well as near vision instantly without conscious accommodation. Notwithstanding the perfect vision enjoyed by a majority of the population, an inability to view objects at infinity, or myopia, is frequently encountered. This visual impairment can be corrected by refractive lens held by glasses frames, wearing contact lens or refractive surgery. In addition, certain human do not focus near vision well. This is known as hyperopia and their vision can also be corrected by conventional refractive techniques. In certain instances of severe lack of accommodation these conventional procedures become undesirable and alternative procedures are needed.

Although a youth of ten years in age has an ability to change the dioptic power by fourteen diopters, this ability gradually decreases with age and by fifty or so the ability of the human eye to accommodate variation in focal length becomes essentially zero. This condition is referred to as presbyopia and a patient often requires correction for both near and far vision. This can be achieved by wearing bifocal glasses or contacts or undergoing refractive surgery for distance and wearing glasses for reading purposes.

In addition to the foregoing more conventional limitations on 20/20 vision in instances of juvenile disease, trauma, and more frequently through age, the natural crystalline lens 32 becomes rigid and opaque to the passage of light. This condition is referred to as a cataract which can be corrected by removal of the lens 32 by a number of techniques, however, the most commonly performed surgery is known as extracapsular extraction. In this procedure, an annular opening in the capsular bag 54 is fashioned about the anterior visual center of the lens, centered by the iris, and then emulsifying and aspirating the hardened lens material. At least one- procedure for phacorinulsification, irrigation and aspiration is disclosed in a U.S. Shearing Pat. No. 5,154,696. Once the natural crystalline lens is removed a bi-convex, fixed focal length optic, of about six millimeters in diameter, is typically fitted into the capsular bag and held in position by radially extending haptics. Although cataract surgery and insertion of an intraocular lens is the most frequently performed surgical procedure in the United States and has achieved a considerable degree of sophistication and success, and intraocular lens is selected with a diopter to achieve for vision and near vision must be corrected by wearing reading glasses.

Finally, retinal disease or damage can impair human vision and one form is known as macular degeneration which usually occurs with advance in age. The symptom of macular degeneration can be alleviated, to a degree, by providing high diopters in the 30 to 70 range such that the rods and cones available to receive sight are utilize to their fullest.

From the foregoing context it will be appreciated that improvements in the eye care industry can be made with respect to correction of vision such as hyperopia presbyopia, replacement of vision following cataract extraction and treatment of retinal dysfunction such as macular degeneration.

Opening, Accommodated Intracular, Lens System

Figure 2:
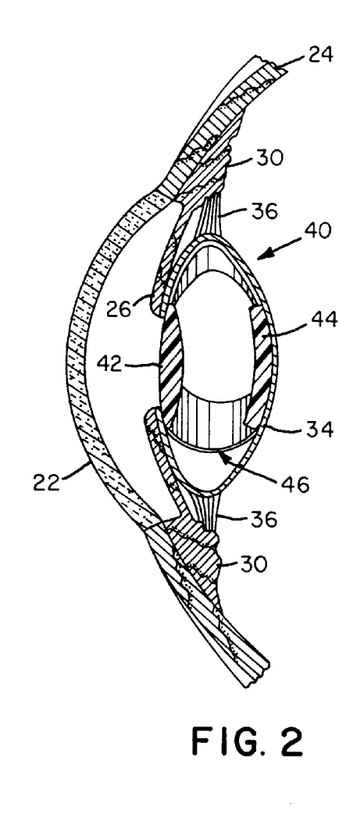
FIG. 2 is a partial cross-sectional view of a human eye as depicted in FIG. 1 where the natural crystalline lens has been replaced with an open accommodative, intraocular lens in accordance with one preferred embodiment of the invention to restore a patient's natural, accommodative, vision following extracapsular surgery.

Referring now to FIG. 2, the subject invention is directed to an open chamber, accommodated, intraocular lens system 40 which is operable to correct and/or eliminate vision impairments of the type described above. The intraocular lens system 40 includes an anterior lens 42, a posterior lens 44 and haptic segments 46 operably connecting the anterior lens 42 with the posterior lens 44. As noted in FIG. 2, the subject intraocular lens system 40 is substantially elliptical in cross-section and operably conforms to the interior three-dimensional surface of the capsular bag 34.

Figure 3:
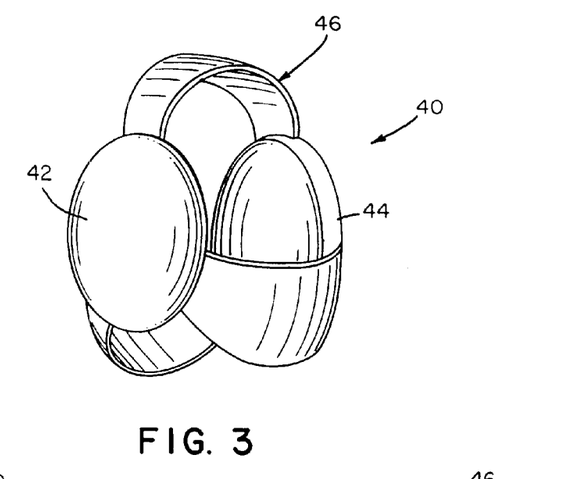
FIG. 3 (note sheet two) is an axonometric view of an open chamber, accommodative, intraocular lens having three elliptically shaped haptics extending between an anterior lens optic and a posterior lens optic in accordance with one preferred embodiment of the invention.
Figure 4:
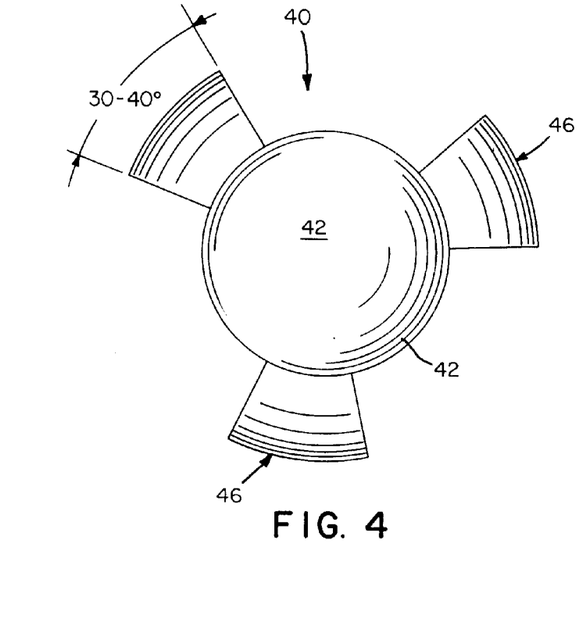
FIG. 4 is a end view of the open chamber intraocular lens system, as depicted in FIG. 3, as viewed along a visual axis 8 the lens as implanted within the capsular bag of a human eye.
Figure 5:
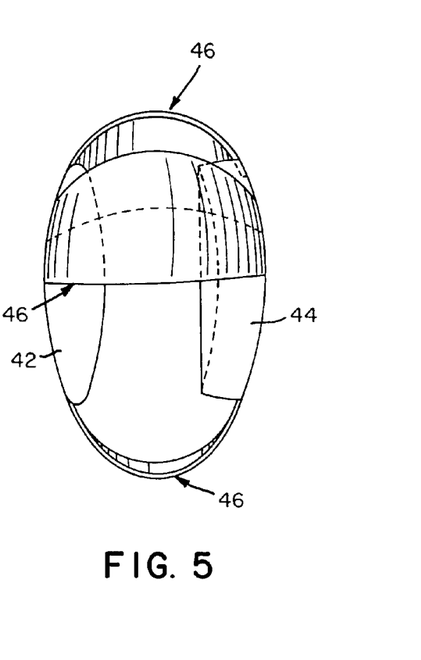
FIG. 5 is a side view of the intraocular lens system, as depicted in FIG. 4, including a preferred form of three equally spaced haptic segments.

Turning to FIGS. 3–5 of the drawings at sheet two, there is shown an axonometric view of a preferred embodiment the subject intraocular lens system 40, a front view, and a side view, respectively. The forward or anterior optic 42 is preferably bi-convex as depicted in FIG. 5 and has a diameter of approximately five millimeters for positioning within a capsular bag 34 immediately behind the iris 26. The power distribution of the anterior and posterior lenses may be varied to suit the needs of the particular patient, however, in a preferred embodiment, the anterior lens is positive and the posterior lens is negative. The posterior lens 44 is in visual, axial alignment with anterior the lens 42 and cooperates with the anterior lens to correct a wearer's vision. In a preferred embodiment, the lens 44 is fashioned in a spherical concavo-convex shape as depicted in FIGS. 3 and 5. Although in a preferred embodiment the anterior and posterior lens combinations are as stated above, other lens couples are contemplated by the subject invention including anterior lens fashioned with concavo-planar, concavo-convex, and convex-concavo configurations. In a similar manner, the posterior lens may also exhibit the range of physical lens formation possibilities of being concave or convex or planar in order to achieve the desired visual result for a particular patient. Lenses are typically fabricated from an optical glass polymethylmethacrylate (PMMA), however other materials may be utilized such as glass, silicone, or acrylics provided visual clarity, refractive ability, and biocompatibility are all maintained.

Figure 6:
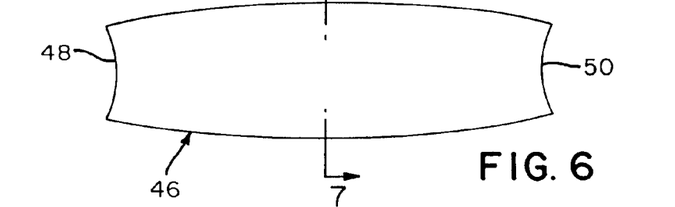
FIG. 6 (note sheet 3) is a plan view of a haptic component disclosing its preferred, general elliptical, configuration.
Figure 7:
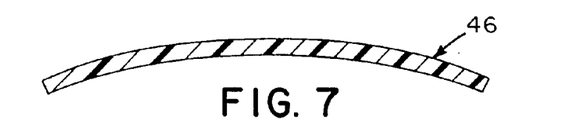
FIG. 7 is a cross-sectional view of the haptic component depicted in FIG. 6 and discloses the arcuate cross-sectional configuration of a haptic element.

In the subject invention, the anterior 42 and posterior 44 lenses coupled are together by a plurality elliptical haptics 46 extending longitudinally in the direction of the line of sight of the lens system. The haptics are connected to the peripheral edges of the anterior and posterior lenses by stalking, integral formation, gluing, or other known techniques and are positioned around the peripheral edges of the lenses in equidistant peripheral locations. In a preferred embodiment, the haptics subtend an angle of thirty to forty degrees as viewed in a direction of line of sight, note FIG. 4, and extend outwardly approximately nine millimeters, in diameter, to approximate the normal internal diameter of the capsular bag of the human eye. As shown in FIG. 6, note sheet three, the haptic 46 is generally elliptical in a plan view and has arcuate end surfaces 48 and 50 for attachment to the periphery of the anterior and posterior lenses as noted above. In cross-section, the haptics 46 are arcuate, note FIGS. 4 and 7, and have a radius of curvature of approximately 4.5 millimeters which enables the haptic to smoothly conform to the interior surface of an evacuated capsular bag.

The haptics 46 are preferably composed of polymethylmethacrylate (PMMA) material which can be molded along with one of the anterior or posterior lenses. In certain instances, it may be desirable to lessen the overall weight of the intraocular lens system within the interior of a patient's eye. For this instance the haptic 46 can be advantageously composed of a polypropylene material having a specific gravity of approximately 0.91 and thus the combination of the PMMA optics and polypropylene haptics offset and the lens system is approximately neutrally buoyant with the aqueous humor. In addition, the haptics can be advantageously composed of an acrylic having a water content of 2 to 30%, a hydroxyethylmethacrylate (HEMA), or polydimethyl siloxanes.

Although three radially extending haptics covering arcs of 30–40 degrees each, such as shown in FIGS. 3–5, constitute a preferred embodiment of the invention, other haptic arrangements of from two to five or more in number are envisioned and can be selected by those of ordinary skill in the art to satisfy the requirement of sufficient flexibility to provide the accommodated focusing of the lens system and simultaneous stiffness to maintain the axial position and orientation of the lens optics.

Figures 8, 9, 10:
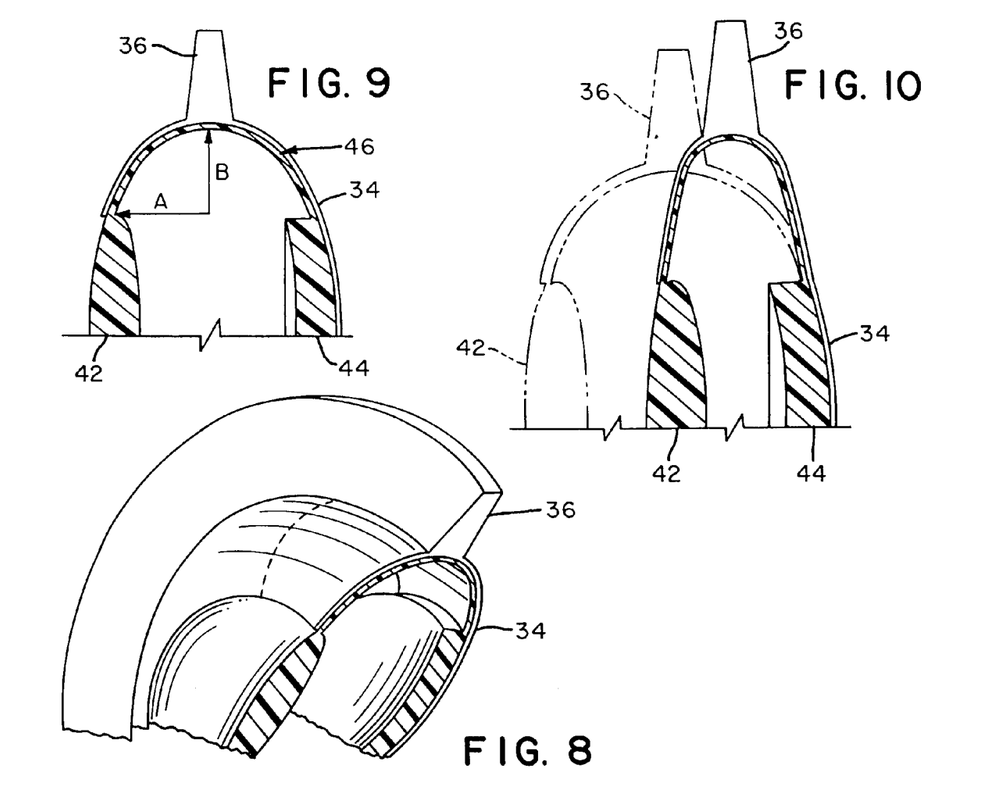
FIG. 8 is a schematic and axonometric illustration of an open accommodative intraocular lens segment in accordance with a preferred embodiment of the invention positioned within the capsular bag of a human eye.
FIG. 9 is a, partial schematic, side view of the accommodative, intraocular lens system, depicted in FIG. 8, in accordance with the invention which discloses the longitudinal elliptical configuration in the line of sight of the lens, of a haptic of the lens system.
FIG. 10 is a schematic illustration of the motion of the open accommodative, intraocular lens system in accordance with a preferred embodiment of the invention, depicted in FIGS. 8 and 9, wherein phantom lines represent a segment of the lens in a natural memory condition following insertion into the capsular bag of a patient's eye, with the patient's ciliary muscle constricted inward to accommodate for near vision, and the solid line segment depicts the position of the lens system when the patient's ciliary muscle relaxes and peripherally expands and stretches the capsular bag outward narrowing the distance between the lens optics to provide accommodative vision at infinity.

Turning to FIGS. 8–10, there will be seen schematic illustrations of a portion of the subject intraocular lens system positioned within a capsular bag. FIG. 9 an elliptical cross-sectional configuration of the haptic 46 wherein the ratio provided by the height A of the ellipse over the length B is 0.96. It has been determined that this ratio is optimum for application of the ciliary muscles and zonula acting upon the capsular bag to provide accommodative vision with the intraocular lens system 40. Although this configuration is preferred, it is envisioned that a more linear arrangement in the form of a triangle with rounded corners may be utilized to advantage provided the material, thickness and configuration remain both flexible and supportive.

Referring again to FIG. 8, a peripheral zone of zonula 36 is schematically which extends peripherally about and is connected to the capsular bag 34. In a condition when the ciliary muscle 30 is relaxed and retracted peripherally outwardly, the zonula 36 will be tensioned outwardly which will pull the equator of the capsular bag 34 into a configuration shown in solid lines in FIG. 10. This position of the capsular bag and the location of the anterior and posterior lenses is optimum for vision at infinity.

When the peripheral ciliary muscles 30 are constricted the hoop dimension is radially lessened which releases tension on the zonula 36 and the capsular bag, biased by the memory shape of the intraocular lens system 40, assumes the condition indicated by phantom lines in FIG. 10. In this, the natural memory shape of the elliptical haptics 46 repositions the anterior lens 42 with respect to the posterior lens 44 axially and is the position used for focusing on near objects down to 250 millimeters. In a preferred embodiment, the subject intraocular lens system cooperates with the ciliary muscle, and zonula and capsular bag to permit a relative axial motion of the anterior lens with respect to the posterior lens of 1.9 millimeters a power correction of approximately 4 diopters. This accommodated motion of the subject intraocular lens system is achieved automatically and seamlessly within the human eye and thus is operable to permanently restore unaided vision.

Although a preferred embodiment of the subject accommodative intraocular lens system has been disclosed and discussed in connection with FIGS. 3–8, other preferred embodiments exist with respect to specific applications such as disclosed in FIGS. 11–14. In this, FIGS. 11 and 12 disclose elliptical haptic, intraocular lens systems utilizing a single anterior lens body 52 which may be used to advantage for the correction of mild to severe myopia (nearsightedness) or hyperopia (farsightedness). In this embodiment, a plurality of elliptical haptics 54 connect at a first portion of peripheral end to the first optic 52 and at a second end to a stabilizing ring 56 positioned in a location posterior to and in axial alignment to the optic 52. This embodiment is operably received within an evacuated capsular bag in a secure and stable manner similar to that shown in FIG. 2.

Figure 12:
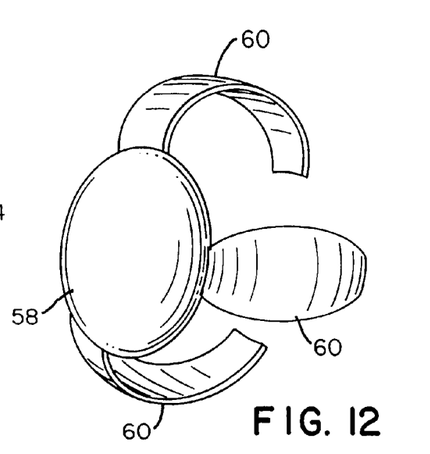
FIG. 12 is an illustration of yet another form of the invention having only an anterior optic and an open posterior area of the intraocular lens system.

In an alternative embodiment of the invention a single lens optic 58, as depicted in FIG. 12, is supported by elliptical haptics 60 having a first end connected to a peripheral rim of the optic and extending to free or distal end positions to a location of posterior proximity. This lens will also snuggly and accommodatively fit within an evacuated capsular bag for use in correction of myopia and hyperopia.

Figure 11:
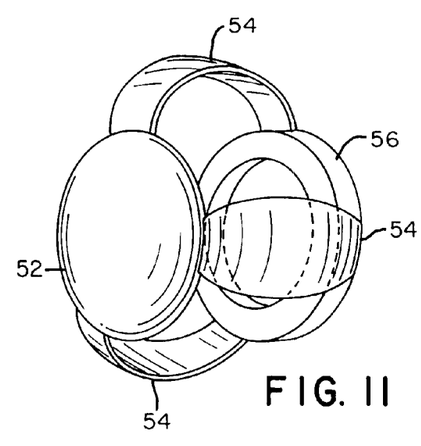
FIG. 11 (note sheet four) is an illustration of another preferred form of the invention where the open, accommodative intraocular lens system includes only one anterior positioned lens optic and a posterior stabilizing ring.

The cross-sectional configuration of the corrective lens 52 of the embodiments depicted in FIGS. 11 and 12 and 58 may be selected for the designated refractive purposes but it is preferred that the lens exhibit a concave-convex, plano-convex, or convex-plano surface configuration as viewed in cross-section.

Figure 13:
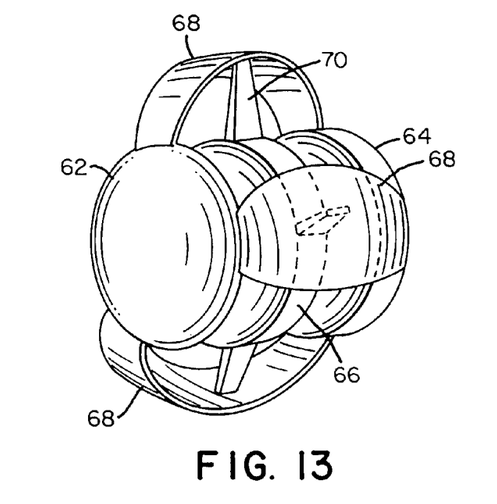
FIG. 13 is an axonometric illustration of another preferred embodiment of the invention where the intraocular lens system includes three lens optics in axial alignment.
Figure 14:
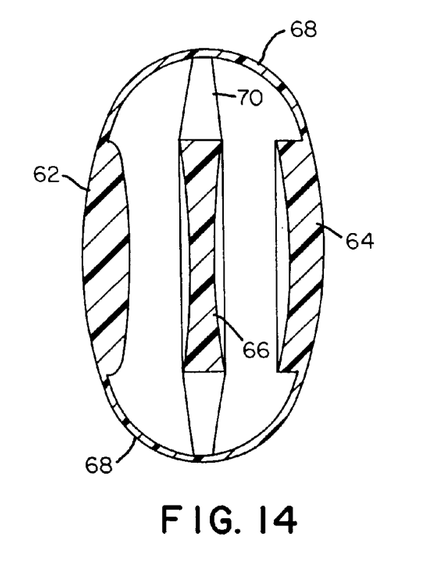
FIG. 14 is a cross-sectional view of a three lens optic system as illustrated in FIG. 13.

In certain instances such as macular degeneration it may be desirable to provide an accommodative intraocular lens system wherein the lens is capable of providing hyper visual corrections of 30–70 diopters. Turning to FIGS. 13 and 14, there is shown an accommodative intraocular lens system including an anterior lens 62, a posterior lens 64, and an intermediate lens 66. An elliptical haptic system 68 surrounds and supports the anterior and posterior lens of the lens system in a manner as previously described. The intermediate lens 66 is supported by radially extending arms 70 which project between the peripheral surface of the interior lens and the intermediate surface of the elliptical haptic 68. This support is illustrated particularly in FIG. 14 which discloses a schematic cross-sectional view taken along section lines taken through the center of adjacent haptics 68 in FIG. 13. The shape and dioptive power of each of the lens 62, 64, and 66 can be varied to suit a particular patient's circumstances. In this embodiment, the anterior lens is the principal moving lens during accommodation, the intermediate lens remains essentially axially stationary, as the support members 70 elongate, with movement of the zonula and the posterior lens may move a small degree but less than the anterior lens 62. The power distribution of each of the lens may be varied to suit the needs of a specific patient, however, if a total power of 28 diopters is required an envisioned distributions would be eight diopters for the anterior lens, ten diopters for the intermediate lens, and four diopters for the posterior lens. Alternatively, the anterior lens may be four diopters, the intermediate lens may be four diopters, and the posterior lens twenty diopters.

Figure 15:
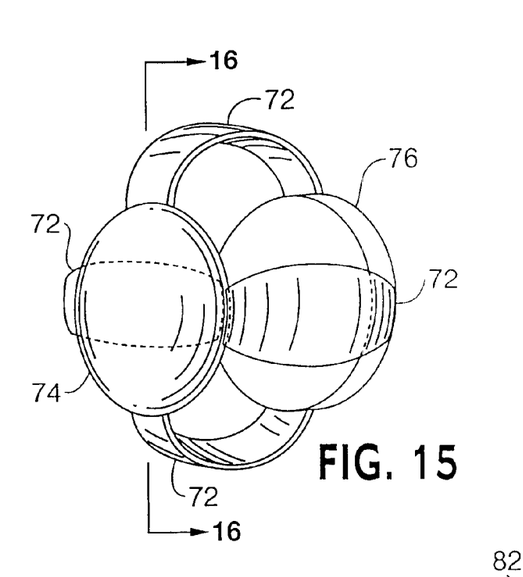
FIG. 15 is a axonometric view of another embodiment of the invention that utilizes four haptic members and a biplanar posterior lens body.
Figure 16:
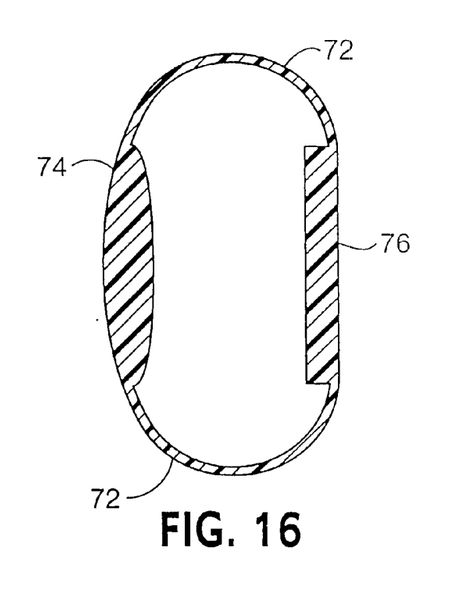
FIG. 16 is a cross-sectional view of the lens depicted in FIG. 15 taken along section lines 16—16.

FIGS. 15 and 16 disclose an intraocular lens system substantially similar to that disclosed in FIGS. 3 and 4 with the exception that four, as opposed to three, haptic elements 72 extend between an anterior lens 74 and a posterior lens optic 76. The haptics 72 are spaced peripherally around the perimeter of the lens optics and are equally spaced as shown. In FIG. 16 a further variation of the posterior lens optic is disclosed. In this the anterior optic comprises a biconvex lens 74 while the posterior lens 76 is biplanar as shown.

Figure 17:
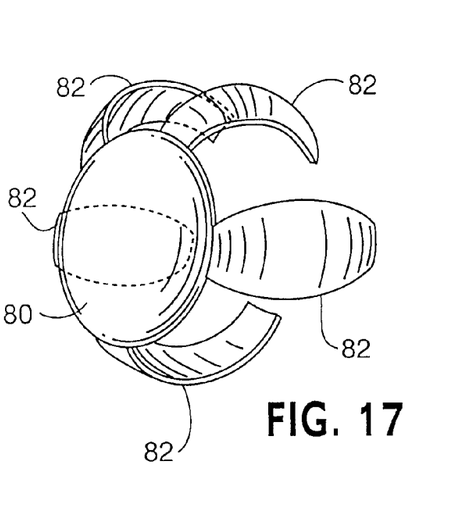
FIG. 17 is yet another embodiment of the invention wherein five haptic members are used to support an anterior lens optic.

Finally, FIG. 17 discloses yet another embodiment of the invention, which is similar to FIG. 12, however, a single lens optic 80 is shown supported by five haptics 82 which are equally spaced about the periphery of the optic. Although in this embodiment the posterior or distal end of the haptics 82 are not attached, it would be possible to use a ring attachment, as shown in FIG. 11, or a posterior lens optic having a cross sectional configuration from a number of designs as shown in FIGS. 2, 8, or 14 of the drawings.

SUMMARY OF MAJOR ADVANTAGES OF THE INVENTION

After reading and understanding the foregoing description of the invention, in conjunction with the drawings, it will be appreciated that several advantages of the subject improved open accommodative, intraocular lens system are achieved.

Without attempting to set forth all of the desirable features of the subject invention an accommodative intraocular lens system including an anterior lens and posterior lens coupled with longitudinally, elliptical haptics operably serve to replace a natural crystalline lens within a patient's evacuated capsular bag and provide an accommodation of four or more diopters suitable to restore bifocal vision to most patients following cataract surgery.

A single, anterior lens embodiment of the invention is advantageously operable to correct both myopia and hyperopia and single or dual lens designs find use in providing full accommodative restoration of vision to presbyopic patients.

In instances of retinal damage or degeneration where high diopter powers enhance vision a three lens embodiment of the invention can be used to produce magnification up to seventy diopters or more.

The elliptical ratio of 0.96 provides a particularly advantageous degree of rigidity and flexibility such that a patient's ciliary muscles, zonula, and natural capsular bag are able to restore a patient's accommodative vision without using other vision correcting devices.

In describing the invention, reference has been made to preferred embodiments and illustrative advantages, those skilled in the art, however, and familiar with the instant disclosure of the subject invention, may recognize additions, deletions, modifications, substitutions and/or other changes which will fall within the purview of the subject invention and claims.

What I claim is:

1. An open accommodative, intraocular lens system operable to be positioned within the interior of an evacuated capsular bag of a human eye, said intraocular lens system comprising:

a first lens optic, operable to be positioned within an anterior portion of an evacuated capsular bag of a human eye, having a central optic axis;

a second lens optic, operable to be positioned within a posterior portion of an evacuated capsular bag of a human eye, having a central optic axis coaxial with said central optic axis of said first lens optic, said second lens optic having a concave, spheric, anterior surface;

a first flexible longitudinally arcuate haptic being arcuate in the direction of said central optic axis and having a first end and a second end, said first haptic extending between said first and second lens optics and directly connected at said first end to said first lens optic and directly connected at said second end to said second lens optic respectively; and at least a second flexible longitudinally arcuate haptic being arcuate in the direction of said central optic axis and having a first end and a second end, said second haptic extending between said first and second lens optics and directly connected at said first end to said first lens optic and directly connected at said second end to said second lens optic respectively, each longitudinally arcuate haptic operable when positioned in an evacuated capsular bag to extend in a generally elliptical curve in longitudinal cross-section and to follow the contour of an interior surface of the evacuated capsular bag said first and second lens optics operable to be supported in general visual axial alignment within an evacuated capsular bag by said first longitudinally arcuate haptic and said at least second longitudinally arcuate haptic abutting against and being supported by interior surfaces of the evacuated capsular bag and the ciliary muscles of a wearer of the intraocular lens system acting through Zonula connected to an exterior surface of the evacuated capsular bag being operable to pull on the evacuated capsular bag and the ciliary muscle and the arcuate haptics being operable to selectively vary the distance between said first lens optic and said second lens optic along the central optic axis of said first lens optic and said second lens optic and facilitate accommodated vision of a wearer of the intraocular lens system.

2. An open accommodative, intraocular lens system as defined in claim 1 wherein said at least a second, arcuate, lens haptic comprises:
   a second and a third, longitudinally arcuate, haptics and said first, second and third haptics being peripherally spaced equally about a rim of said first and second lens optics.

3. An open accommodative, intraocular lens system as defined in claim 2 wherein:
   said first, second and third, longitudinally arcuate, haptics when viewed in a direction normal to an anterior face of said first lens optic, extend outwardly from a periphery of the first lens optic at an angle of approximately 30 to 40 degrees and said haptics are equally spaced about the periphery of the optic.

4. An open accommodative, intraocular lens system as defined in claim 3 wherein:
   said first, second and third, longitudinally arcuate, haptics when viewed in longitudinally cross-section are elliptical with a ratio of ellipse of approximately 0.96.

5. An open accommodative, intraocular lens system as defined in claim 3 wherein:
   the cross-sectional configuration of each of said first, second and third haptics transverse to the direction of said optic axes is substantially a circular arc and having a radius of curvature of approximately 4.5 mm.

6. An open accommodative, intraocular lens system as defined in claim 1 wherein said at least a second, arcuate, lens haptic comprises:
   second, third and fourth, longitudinally arcuate, haptics; and
   said first, second, third and fourth haptics being peripherally spaced about peripheral rims of said first and second lens optics.

7. An open accommodative, intraocular lens system as defined in claim 1 wherein said at least a second, arcuate, lens haptic comprises:
   second, third, fourth and fifth, longitudinally arcuate, haptics; and
   said first, second, third, fourth and fifth haptics being peripherally spaced about peripheral rims of said first and second lens optics.

8. An open accommodative, intraocular lens system as defined in claim 1 wherein said at least a second, arcuate lens haptic comprises:
   two, or more, longitudinally arcuate, haptics each having a first end and a second end, each of said longitudinally arcuate haptics extending between and connected at said first ends to spaced peripheral portions of said first lens optic and connected at said second ends to spaced peripheral portions of said second optic.

9. An open accommodative, intraocular lens system as defined in claim 1 wherein:
   said first, longitudinally arcuate, haptic and said at least a second, longitudinally arcuate, haptic being also arcuate transverse to the direction of said optic axes so as to operably fit smoothly within the interior of and abut against the interior surfaces of the evacuated capsular bag of a wearer of the intraocular lens system.

10. An open accommodative, intraocular lens system as defined in claim 1 wherein:
    said first, longitudinally arcuate, haptic and said at least a second, longitudinally arcuate, haptic being generally elliptical in a planar perspective prior to attachment to periphery positions of the first and second lens optics.

11. An open accommodative, intraocular lens system as defied in claim 1 wherein:
    said fist, longitudinally arcuate, haptic and said at least a second, longitudinally arcuate, haptic are generally rectangular in a planar perspective prior to attachment to periphery positions of the first and second lens optics.

12. An open accommodative, intraocular lens system as defined in claim 1 wherein:
    said first and second lens optics and said first and at least a second lens haptics are all composed of polymethylmethacrylate material.

13. An open accommodative, intraocular lens system as defined in claim 1 wherein:
    said first and second lens optics are composed of polymethylmethacrylate material; and
    said first and said at least a second lens haptics are all composed of polypropylene having a specific gravity of less than 1.0 and thus providing offset buoyancy for the lens optics when the intraocular lens is positioned within the aqueous humor of a human eye.

14. An open accommodative, intraocular lens system as defined in claim 1 wherein:
    said first and second lens optics are each composed of polymethylmethacrylate material; and
    said first and at least a second haptics are composed of an acrylic material having a water content of between 2% and 30%.

15. An open accommodative, intraocular lens system as defined in claim 1 wherein:
    said first and second lens optics are each composed of polymethylmethacrylate material; and
    said first and at least a second haptics are composed of hydroxyethylmethacrylate.

16. An open accommodative, intraocular lens system as defined in claim 1 wherein:
    said first and second lens optics are each composed of polymethylmethacrylate material; and
    said first and at least a second haptics are composed of polydimethyl siloxanes.

17. An open chamber, accommodative, intraocular lens system as defined in claim 1 wherein:
    said first and second lens optics are each composed of polymethylmethacrylate material; and
    said first and at least a second longitudinally arcuate haptic segments are composed of an acrylic material having a specific gravity less than one so as to provide offsetting positive buoyancy with respect to the negative buoyancy of the lens optics.

18. An open chamber, accommodative, intraocular lens system operable to be positioned within the interior of an evacuated capsular bag of a human eye, as defined in claim 1 wherein:

said first lens optic comprises a bi-convex lens having a convex, spheric, anterior surface and a convex, spheric, posterior surface as viewed from the perspective of the lens being placed within an evacuated capsular bag of a wearer's eyes; and said second lens optic comprises a concave-convex lens having a concave, spheric, anterior surface and a convex, spheric, posterior surface as viewed from the perspective of the lens being placed within the evacuated capsular bag of a wearer's eyes.

19. An open accommodative, intraocular lens system operable to be positioned within the interior of an evacuated capsular bag of a human eye, as defined in claim 1 wherein:

said first lens optic comprises a bi-convex lens having a convex, spheric, anterior surface and a convex, spheric, posterior surface, as viewed from the perspective of the lens being placed within an evacuated capsular bag of a wearer's eye; and said second lens optic comprises a concave-planar lens having a concave, spheric, anterior surface and a planar posterior surface, as viewed from the perspective of the lens being placed within an evacuated capsular bag of a wearer's eye.

20. An open accommodative, intraocular lens system operable to be positioned within the interior of an evacuated capsular bag of a human eye, as defined in claim 1 wherein:

said first lens optic comprises a bi-convex lens having a convex, spheric, anterior surface and a convex, spheric, posterior surface, as viewed from the perspective of the lens being placed within an evacuated capsular bag of a wearer's eye; and said second lens optic having biplanar anterior and posterior surfaces and thus providing no refraction of light passing through the second lens from curvature of the lens optics surfaces.

21. An open accommodative, intraocular lens system operable to be positioned within the interior of an evacuated capsular bag of a human eye, as defined in claim 1 wherein:

axial spacing of the first lens optic with respect to the second lens optic, when positioned within an evacuated capsular bag of a human eye, is such that the ciliary muscle of the wearer is operable to effect an accommodative axial, line of sight, displacement of the first optic lens with respect to the second optic of approximately 2 mm.

22. An open accommodative, intraocular lens system operable to be positioned within the interior of an evacuated capsular bag of a human eye, as defined in claim 1 wherein:

axial spacing of the first lens optic with respect to the second lens optic, when positioned within an evacuated capsular bag of a human eye, is such that the ciliary muscle of the wearer is operable to effect a visual accommodation of four diopters.

23. An open accommodative, intraocular lens system as defined in claim 1 wherein:

the optic power of said first lens optic is positive and said second lens optic is negative.

24. An open accommodative, intraocular lens system operable to be positioned within the interior of an evacuated capsular bag of a human eye, said intraocular lens system comprising:

an anterior lens optic, operable to be positioned at an anterior portion of an evacuated capsular bag of a human eye, having a central line of sight axis;

a posterior lens optic, operable to be positioned at an posterior portion of an evacuated capsular bag of a human eye, having a central line of sight axis coaxial with said central line of sight axis of said anterior lens optic, said posterior lens optic having a concave, spheric, anterior surface;

a first haptic means connected directly to and longitudinally between said anterior lens optic and said posterior lens optic in the direction of said line of sight axes of the anterior and posterior lens optics for partially supporting said lens optics within the capsular bag and permitting relative axial motion of said anterior lens optic with respect to said posterior lens optic while maintaining said posterior lens optic in an essentially stationary position; and at least a second haptic means connected directly to and longitudinally between said anterior lens optic and said posterior lens optic in the direction of said line of sight axes of the anterior and posterior lens optics for partially supporting said lens optics within the capsular bag and permitting relative axial motion of said anterior lens optic with respect to said posterior lens optic while maintaining said posterior lens optic in an essentially stationary position to provide accommodative vision to a patient; the haptic means being flexible and operable to extend in a generally elliptical curve in longitudinal cross-section when positioned in an evacuated capsular bag and to follow the contour of the interior surface of the evacuated capsular bag.

25. An open accommodative, intraocular lens system operable to be positioned within an evacuated capsular bag of a human eye, as defined in claim 24 wherein said at least a second haptic means comprises:

a second and a third haptic means connected to and longitudinally between said anterior lens optic and said posterior lens optic.

26. An open accommodative, intraocular lens system operable to be positioned within an evacuated capsular bag of a human eye, as defined in claim 25 wherein:

said first, second, and third haptic means are shaped in the form of a partial ellipse in longitudinal cross-section and the ratio of the ellipse is approximately 0.96.

27. An open accommodative, intraocular lens system operable to be positioned within an evacuated capsular bag of a human eye, as defined in claim 26 wherein:

the cross-sectional configuration of each of said first, second and third haptic means transverse to said line of sight axes is substantially a circular arc and having a radius of curvature of approximately 4.5 mm.

28. An open accommodative, intraocular lens system operable to be positioned within an evacuated capsular bag of a human eye, as defined in claim 27 wherein:

said first, second and third haptic means, when viewed along the line of sight of the anterior lens optic, extends outwardly at an angle of approximately 40 degrees and the spacing between said first, second and third haptic means being approximately 80 degrees.

29. An open accommodative, intraocular lens system operable to be positioned within an evacuated capsular bag of a human eye following extracapsular extraction of a natural crystalline lens, said intraocular lens system comprising:

an anterior refractive lens optic, operable to be positioned at an anterior portion of an evacuated capsular bag of a human eye, said anterior refractive lens optic having a line of sight central longitudinal axis;

a first haptic having a first end and being connected at said first end directly to a peripheral portion of said anterior refractive lens optic and a second end and said haptic being flexible and extending in a generally elliptical curve in a longitudinal cross-section and being operable to follow the interior contour of an evacuated capsular bag of a human eye from an anterior portion to a posterior portion of a capsular bag of a human eye; and at least a second haptic having a first end and being connected at said first end to a peripheral portion of said anterior refractive lens optic and a second end, and said haptic being flexible and extending in a generally elliptical curve in longitudinal cross-section, and being operable to follow the interior contour of an evacuated capsular bag of a human eye from an anterior portion to a posterior portion of a capsular bag of a human eye and said first haptic and said at least a second haptic extending in the direction of said line of sight central longitudinal axis to form an open elliptical shaped haptic accommodating support for the anterior refractive optic lens operable to be positioned within an evacuated capsular bag of a human eye.

30. An open accommodative, intraocular lens system operable to be positioned within an evacuated capsular bag of a human eye following extracapsular extraction of a natural crystalline lens as defined in claim 29 wherein:
said anterior refractive lens is concave-convex in cross-section.

31. An open accommodative, intraocular lens system operable to be positioned within an evacuated capsular bag of a human eye following extracapsular extraction of a natural crystalline lens as deemed in claim 29 wherein:
said anterior refractive lens is plano-convex in cross-section.

32. An open accommodative, intraocular lens system operable to be positioned within an evacuated capsular bag of a human eye following extracapsular extraction of a natural crystalline lens as defined in claim 29 wherein:
said anterior refractive lens is convex-plano in cross-section.

33. An open accommodative, intraocular lens system operable to be positioned within an evacuated capsular bag of a human eye following extracapsular extraction of a natural crystalline lens as defined in claim 29 wherein:
the second ends of said haptics are each joined to a retaining ring at a posterior position of the intraocular lens system and said retaining ring operably abuts against a posterior surface of the capsular bag upon insertion of the intraocular lens within a human eye.

34. An open accommodative, intraocular lens system operable to be positioned within an evacuated capsular bag of a human eye following extracapsular extraction of a natural crystalline lens as defined in claim 33 wherein:
said at least a second haptic comprises a second and a third elliptical haptic spaced about the periphery of said anterior lens optic.

35. An open accommodative, intraocular lens system operable to be positioned within an evacuated capsular bag of a human eye following extracapsular extraction of a natural crystalline lens as defined in claim 34 wherein:
said first, second, and third haptics are shaped in the form of a partial ellipse in longitudinal cross-section and the ratio of the ellipse is approximately 0.96.

36. An open accommodative, intraocular lens system operable to be positioned within an evacuated capsular bag of a human eye following extracapsular extraction of a natural crystalline lens as defined in claim 35 wherein:
the transverse cross-sectional configuration of each of said first, second and third haptics is substantially a circular arc and having a radius of curvature of approximately 4.5 mm.

37. An open accommodative, intraocular lens system operable to be positioned within an evacuated capsular bag of a human eye following extracapsular extraction of a natural crystalline lens as defined in claim 36 wherein: said first, second and third haptics, when viewed along the line of sight of the anterior lens optic, extends outwardly at an angle of approximately 30 to 40 degrees and said haptic segments being spaced equally said optic lens.

38. An open accommodative, intraocular lens system operable to be positioned within an evacuated capsular bag of a human eye following extracapsular extraction of a natural crystalline lens as defined in claim 29 wherein:
the second ends of said haptics are each free and extend to a posterior position of the intraocular lens system and being operable to abut against a posterior surface of the capsular bag upon insertion of the intraocular lens within a human eye.

39. An open accommodative, intraocular lens system as defined in claim 29 wherein:
said first haptic and said at least a second haptic are generally elliptical in a planar perspective prior to attachment to the peripheral portions of aid anterior refractive lens optic.

40. An open accommodative, intraocular lens system as defined in claim 29 wherein:
said anterior refractive lens optic is concavo-planar in cross-section.

41. An open accommodative, intraocular lens system as defined in claim 29 wherein:
said anterior refractive lens optic is bi-convex in cross-section.

42. An open accommodative, intraocular lens system as defined in claim 29 wherein:
said anterior refractive lens optic is convex-concavo in cross-section.

43. An open accommodative, intraocular lens system as defined in claim 29 wherein:
said anterior refractive lens optic is concavo-concavo in cross-section. said first, second and third haptics, when viewed along the line of sight of the anterior lens optic, extends outwardly at an angle of approximately 30 to 40 degrees and said haptic segments being spaced equally about said lens optic.

44. An open accommodative, intraocular lens system as defined in claim 29 wherein:
said anterior refractive lens optic is composed of a silicone material.

45. An open accommodative, intraocular lens system as defined in claim 44 wherein:
said anterior refractive lens optic is integral with said first haptic and said at least a second haptic.

46. An open accommodative, intraocular lens system as defined in claim 29 wherein:
said anterior refractive lens optic is composed of a polymethylmthacrylate material.

47. An open accommodative, intraocular lens system as defined in claim 29 wherein:
said anterior refractive lens optic is composed of an acrylic material.

48. An open accommodative, intraocular lens system operable to be positioned within an evacuated capsular bag of a human eye following extracapsular extraction of a natural crystalline lens, said intraocular lens system. comprising:
- an anterior lens optic operable to be positioned within an anterior portion of an evacuated capsular bag of a human eye and having a central line of sight axis;
- a posterior lens optic operable to be positioned at an posterior portion of an evacuated capsular bag of a human eye and having a central line of sight axis coaxial with said central line of sight axis of said anterior lens optic, said posterior lens optic having a concave, spheric, anterior surface;
- an intermediate lens optic positioned between and in visual axial alignment with said anterior and posterior lens optics;
- a first haptic means connected directly to said anterior lens optic, said posterior lens optic and said intermediate lens optic and being operable for supporting said lens optics within the capsular bag and permitting relative accommodative motion of said anterior lens optic with respect to said posterior lens optic; and
- at least a second haptic means connected directly to said anterior lens optic, said posterior lens optic and said intermediate lens optic and being operable for cooperating with said first haptic means for supporting said lens optics within the capsular bag and permitting relative accommodative motion of said anterior lens optic with respect to said posterior lens optic; each haptic means being flexible and operable when positioned in a evacuated capsular bag to extend in a generally elliptical curve in longitudinal cross-section and to follow the contour of the interior surface of the evacuated capsular bag.

49. An open accommodative, intraocular lens system operable to be positioned within an evacuated capsular bag of a human eye following extracapsular extraction of a natural crystalline lens as defined in claim 48 wherein:
- said first haptic means comprises an elliptical haptic; and
- said at least a second haptic means comprises a second and a third elliptical haptic, said first, second and third haptics being spaced about a periphery of said anterior and posterior lens optics.

50. An open accommodative, intraocular lens system operable to be positioned within an evacuated capsular bag of a human eye following extracapsular extraction of a natural crystalline lens as defined in claim 49 wherein:
- said first, second and third haptics, when viewed along the line of sight of the anterior lens, extends outwardly at an angle of approximately 40 degrees and the spacing between said first, second and third haptics segments being approximately 80 degrees.

51. An open accommodative, intraocular lens system operable to be positioned within an evacuated capsular bag of a human eye following extracapsular extraction of a natural crystalline lens as defined in claim 50 wherein:
- said first, second, and third haptics are shaped in the form of a partial ellipse in longitudinal cross-section taken along the central line of sight axes of said lenses and the ratio of the ellipse is approximately 0.96.

52. An open accommodative, intraocular lens system operable to be positioned within an evacuated capsular bag of a human eye following extracapsular extraction of a natural crystalline lens as defined in claim 51 wherein:
- the cross-sectional configuration of each of said first, second and third haptics, taken transverse to the direction of the line of sight of said lens optics, forming substantially a circular arc and having a radius of curvature of approximately 4.5 mm.

53. A method for achieving accommodative vision following an extracapsular operative procedure for removing a patient's natural crystalline lens, said method comprising the steps of:
- inserting into the evacuated capsular bag of each eye an accommodative intraocular lens system including at least one lens optic having a line of sight central longitudinal axis and positioning said at least one lens optic in, an anterior portion of an evacuated capsular bag of a human eye and a plurality of flexible haptics forming an open lens system, said haptics operable when positioned in the evacuated capsular bag to extend in a generally elliptical curve in longitudinal cross-section and having an exterior configuration approximating the shape of the interior surfaces of the evacuated capsular bag from an anterior portion to a posterior portion of an evacuated capsular bag of a human eye;
- providing for near vision acuity by the natural memory state of the haptics of the intraocular lens system; and
- providing accommodative far vision acuity by tensioning the Zonula connected to the equator periphery of the evacuated capsular bag and thereby moving the lens along the line of sight axis within the eye of a wearer of the accommodative intraocular lens system.

54. The method for achieving accommodative vision following an extracapsular operative procedure for removing a patient's natural crystalline lens as defined in claim 53 wherein:
- said method being operable for refractive correction of a patient's myopia.

55. A method for achieving accommodative vision following an extracapsular operative procedure for removing a patient's natural crystalline lens as defined in claim 53 wherein:
- said step of inserting includes inserting a first and a second lens optic into the evacuated capsular bag in an anterior position and a posterior position respectively; and
- providing accommodative far vision comprises moving the anterior lens optic along the axis of sight toward the posterior lens within the interior of the evacuated capsular bag.

56. A method for achieving accommodative vision following an extracapsular operative procedure for removing a patient's natural crystalline lens as defined in claim 55 wherein:
- said method being operable for restoring a patient's vision following cataract extraction.

57. A method for achieving accommodative vision following an extracapsular operative procedure for removing a patient's natural crystalline lens as defined in claim 55 wherein:
- said method being operable for restoring a patient's vision to correct for presbyopia.

58. A method for achieving accommodative vision following an extracapsular operative procedure for removing a patient's natural crystalline lens as defined in claim 55 wherein:
- said step of inserting further includes inserting a third lens optic into the evacuated capsular bag in a position between said first and second lens optics; and
- said method being operable for providing a range of powers of 30 to 70 diopters for facilitating a patient's vision impaired by macular degeneration.

* * * * *